United States Patent
Levy et al.

(10) Patent No.: US 9,804,172 B2
(45) Date of Patent: Oct. 31, 2017

(54) SOLUBLE ST2 AS A MARKER FOR RISK OF MORTALITY IN HIV-INFECTED SUBJECTS

(71) Applicants: INSTITUT NATIONAL DE LA SANTE ET DE LA RECHERCHE MEDICALE (INSERM), Paris (FR); UNIVERSITE PARIS-EST CRETEIL VAL DE MARNE, Creteil (FR)

(72) Inventors: Yves Levy, Creteil (FR); Sophie Hue, Creteil (FR); Jean-Daniel Lelievre, Creteil (FR)

(73) Assignees: INSTITUT NATIONAL DE LA SANTE ET DE LA RECHERCHE MEDICALE (INSERM), Paris (FR); UNIVERSITE PARIS-EST CRETEIL VAL DE MARNE, Creteil (FR); ASSISTANCE PUBLIQUE—HOPITAUX DE PARIS, Paris 4ème (FR)

( * ) Notice: Subject to any disclaimer, the term of this patent is extended or adjusted under 35 U.S.C. 154(b) by 0 days.

(21) Appl. No.: 14/365,340

(22) PCT Filed: Dec. 14, 2012

(86) PCT No.: PCT/EP2012/075554
§ 371 (c)(1),
(2) Date: Jun. 13, 2014

(87) PCT Pub. No.: WO2013/092412
PCT Pub. Date: Jun. 27, 2013

(65) Prior Publication Data
US 2014/0349324 A1 Nov. 27, 2014

Related U.S. Application Data

(63) Continuation of application No. 13/328,406, filed on Dec. 16, 2011, now abandoned.

(51) Int. Cl.
*G01N 33/53* (2006.01)
*G01N 33/68* (2006.01)

(52) U.S. Cl.
CPC ..... *G01N 33/6866* (2013.01); *G01N 33/6869* (2013.01); *G01N 2333/7155* (2013.01); *G01N 2800/32* (2013.01)

(58) Field of Classification Search
None
See application file for complete search history.

(56) References Cited

U.S. PATENT DOCUMENTS

| 9,057,733 B2 * | 6/2015 | Snider | C12Q 1/6883 |
| 2010/0159607 A1 * | 6/2010 | Lee | C12Q 1/6883 436/86 |
| 2015/0153360 A1 * | 6/2015 | Lee | C12Q 1/6883 424/158.1 |

* cited by examiner

*Primary Examiner* — Michael Pak
(74) *Attorney, Agent, or Firm* — Whitham, Curtis & Cook, P.C.

(57) ABSTRACT

The present invention relates to materials and methods concerning the IL-1 receptor family protein ST2. Use of soluble ST2 as a marker for cardiovascular disease or disease outcome is provided, in particular as a marker of the risk of mortality.

6 Claims, 2 Drawing Sheets

SOLUBLE ST2 AS A MARKER FOR RISK OF MORTALITY IN HIV-INFECTED SUBJECTS

FIELD OF THE INVENTION

The present invention relates to materials and methods concerning the IL-1 receptor family protein ST2. Use of soluble ST2 as a marker for cardiovascular disease or disease outcome is provided, in particular as a marker of the risk of mortality.

BACKGROUND

ST2 is a member of the IL-1 receptor family having 38% amino acid homology to the IL-1R. Due to differential splicing, the ST2 gene encodes at least four isoforms of protein, a soluble form (sST2), a membrane bound form (ST2L) and 2 variant ST2s (Oshikawa et al, 2001, Am J Respir Drit Care Med 164: 277). ST2 gene expression is widespread but the membrane bound form is most highly expressed on mast cells and Th2 cells. IL-33 was recently identified as the ligand for ST2. IL-33 binds a heterodimeric receptor complex consisting of ST2 and the ubiquitously expresses IL-1R accessory receptor protein (IL-1R-AP) and activates several signaling proteins including, NFκB and MAP kinases such as p38 and JNK. The IL-33/ST2 axis is involved in the promotion and maintenance of allergic inflammation via a number of cell types that include Th2 cells, mast cells and basophil, and structural cells such as airway epithelium and smooth muscle cells.

IL-33 mRNA is expressed by multiple organs and cell types in human and mice. At the protein level, IL-33 is mainly expressed by fibroblasts, epithelial cells and endothelial cells, particularly in high endothelial venules. However, in the absence of pro-inflammatory stimuli, IL-33 localizes to the nucleus. IL-33 is specifically released during necrotic cell death, which is thought to be associated with tissue damage during trauma or infection. Under these conditions, extracellular IL-33 may engage the ST2 receptor on mast cells and other immune cells in order to alert the immune system of tissue damage and infection and to promote the initiation of the healing responses. Because IL-33 is released by necrotic, but not apoptotic, cells and can recruit and activate immune cells, it has been suggested that IL-33 is an 'alarmin' or an endogenous danger signal as HMGB1 and IL-1α and therefore, IL-33 is proposed to have an important role in sensing damage in various infectious and inflammatory disease.

IL33/ST2 signalling is believed to function as a paracrine system to protect the heart from the maladaptive remodeling induced by mechanical stressors such as myocardial infarction (MI) and hypertension. The transcript for ST2 is markedly upregulated in mechanically-stimulated cardiomyocytes in vitro, and the cardiac ST2 transcript and serum ST2 protein are increased following the induction of myocardial infarction in vivo. A physiological function of sST2 is suggested by the protective effect of IL33 administration in cardiac overload, mediated by reducing cardiomyocyte hypertrophy and leading to reduced cardiac dysfunction and improved survival.

In contrast, sST2 inhibits the action of IL-33 by acting as a decoy receptor, and serum concentration of sST2 has been shown to be correlated to structural and functional cardiac changes consistent with the remodelling in patients with heart failure. A study analysed serum levels of sST2 in patients with non-ischaemic congestive heart failure (CHF) defined as a reduced left ventricular ejection fraction. An increase in serum ST2 levels was found to independently predict the risk for reaching a subsequent endpoint of mortality or cardiac transplantation in a multivariate model that included measurements of BNP (brain natriuretic peptide). In In mice with germline deletion of ApoE (a key factor in cholesterol metabolism, deficiency of which leads to spontaneous hypercholesterolemia and atherosclerotic disease), IL-33 reduced aortic atherosclerotic plaque development and induced serum levels of antibodies to oxidized low density lipoprotein (oxLDL), which are atheroprotective. Conversely, administration of the decoy receptor, sST2 resulted in a significantly higher aortic plaque burden compared with control mice. Thus, in both heart failure and atherosclerosis, IL-33 signalling appears beneficial, and sST2 might act as a decoy receptor to reduce IL-33 signalling through the ST2L receptor.

Advances in management of HIV disease and antiretroviral therapy (ART) during the last decade have led to prolonged disease free survival in a majority of subjects with HIV infection. Cardiovascular disease (CVD) is now a leading cause of death among HIV-infected patients. There is evidence that the rate of acute myocardial infarction (MI) in HIV-infected patients may be higher than in the general population even after adjustment for anthropometric factors, race, hypertension, diabetes and dyslipidemia. Because ST2/IL-33 signalling is involved in cardiovascular disease and inflammatory disease, the inventors examined whether sST2 levels are increased in HIV-infected patients in a first cross sectional study. Subsequently, they aimed to quantify the risk of CVD events associated with serum sST2 at baseline in the Strategies for Management of Antiretroviral Therapy (SMART) study. Their work was presented at the $6^{th}$ IAS conference on HIV pathogenesis, treatment and prevention, 17 Jul. 2011

DESCRIPTION OF THE INVENTION

The inventors have found that expression of sST2 is higher in HIV-infected subjects than in the general population. They have also found that, in HIV-infected subjects, sST2 expression is correlated with the risk of death, in particular the risk of death from cardiovascular events, although the risk of developing cardiovascular disease is not related to sST2 expression.

Thus, in one aspect, the invention provides a method of predicting the risk of mortality of a subject, preferably an HIV-infected subject, comprising detecting sST2 in a biological sample from said subject. In a preferred embodiment, said method comprises:

(i) determining the level of sST2 in a biological sample from said subject; and (ii) comparing said level of sST2 with a control level;

wherein the level of sST2 in the subject sample compared to the control sample is indicative of the risk of mortality. Typically, a level of sST2 in the sample which is higher than that of the control is indicative of an increased risk of mortality. In some embodiments, the risk of mortality is risk of death following a cardiovascular event. In some embodiments, the risk of mortality is risk of death from any cause. In certain embodiments, the risk of death is risk of death from allergy, asthmas and/or chronic lung disease. The risk of mortality may be, for example, risk of death within one year.

In some embodiments, the subject has pre-existing cardiovascular disease and/or has experienced at least one cardiovascular event. In other embodiments, the subject has no-pre-existing cardiovascular disease and/or has never experienced a cardiovascular event.

Also provided is a method of prognosis of disease in an HIV-infected subject, said method comprising detecting sST2 in a biological sample from said subject. In a preferred embodiment, said method comprises:

(i) determining the level of sST2 in a biological sample from said subject; and (ii) comparing said level of sST2 with a control level;

wherein the level of sST2 in the subject sample compared to the control sample is prognostic of the course of the disease. Typically, a level of sST2 in the sample which is higher than that of the control is indicative of a poor prognosis.

In some embodiments, the disease is cardiovascular disease. In other embodiments, the disease is allergy, asthma or chronic lung disease.

In preferred embodiments, the subject has not yet commenced anti-HIV therapy, for example antiretroviral therapy.

The control level may be, for example, a control standard level obtained from a healthy subject, a group of healthy subjects, or a randomly selected representative sample of subjects. Preferably, the subjects are human subjects.

The invention further provides a method of monitoring the efficacy of treatment of a disease, comprising monitoring sST2 expression during the treatment. A reduction in sST2 level over the course of the treatment may be indicative of the efficacy of the treatment. Preferably, the treatment is treatment of a cardiovascular disease. Alternatively, the disease may be allergy, asthma or chronic lung disease.

The invention further provides a method of selecting a suitable treatment for a disease, based on the expression of sST2 in a biological sample from a subject, preferably an HIV-infected subject. For example, where an elevated level of sST2 is detected in a subject compared to a control, an aggressive treatment may be selected. Conversely, where sST2 levels are not elevated, a more conservative treatment may be selected. In some embodiments, the disease is cardiovascular disease. In other embodiments, the disease is allergy, asthma or chronic lung disease.

Also provided is a method of treatment of disease comprising administering an sST2 antagonist to a patient in need thereof. Preferably, said sST2 antagonist is an inhibitor of the ability of sST2 to interact with IL33. Preferably, said patient is a patient who is HIV-infected. In some embodiments, the disease is cardiovascular disease. In other embodiments, the disease is allergy, asthma or chronic lung disease.

sST2 and Variants

ST2, also known as interleukin-1 receptor-like 1 or IL1RL1, is a protein encoded by the IL1RL1 gene in humans. At least four isoforms of ST2 are known: a soluble form (sST2), a membrane bound form (ST2L) and 2 variants (ST2V and ST2LV), as described in Tominaga et al (1989), FEBS Lett 258:301-304; Yanagisawa et al (1993), FEBS Lett 318:83-87; Tominaga et al (1992), Biochim Biophys Acta 1171:215-218; and Tominaga et al (1999), Biochem Biophys res Comm 264:14-18.

The amino acid sequence of full-length human sST2 is shown in SEQ ID No 2. The amino acid sequence of full-length human membrane bound ST2 is shown in SEQ ID No 1. The amino acid sequence of sST2 is publicly available under GenBank accession no NP_003847.2, and the nucleic acid sequence of the sST2 mRNA is available under GenBank accession no NM_003856.2. The UNiProt identifier of ST2 is Q01638; the transmembrane form is therein referred to as Isoform A and the soluble form as Isoform B.

Reference to sST2 herein may also encompass variant forms of the protein. In particular, naturally occurring variant sequences and fragments are encompassed by the term. Four isoforms of ST2 exist-sST2, ST2L, ST2V and ST2LV. The soluble ST2 and the transmembrane (ST2L) forms arise from a dual promoter system to drive differential expression. sST2 lacks the transmembrane and cytoplasmic domains contained within the structure of ST2L and includes a unique nine amino-acid C-terminal sequence. The overall structure of ST2L is similar to the structure of the type I IL-1 receptors, which are comprised of an extracellular domain of three linked immunoglobulin-like motifs, a transmembrane segment and a TIR cytoplasmic domain. ST2V and ST2LV are 2 splice variants of ST2. Loss of the third immunoglobulin motif and alternatives splicing in the C-terminal portion of ST2, resulting in a unique hydrophobic tail, produces ST2V, whereas alternative splicing, leading to deletion of the transmembrane domain of ST2L, produces ST2LV.

Variant proteins may be naturally occurring variants, such as splice variants and alleles. Variations in amino acid sequence may be introduced by substitution, deletion or insertion of one or more codons into the nucleic acid sequence encoding the protein that results in a change in the amino acid sequence of the protein. Optionally the variation is by substitution of 1, 2, 3, 4, 5, 6, 7, 8, 9, 10, 11, 12, 13, 14, 15, 16, 17, 18, 19, 20 or more amino acids with any other amino acid in the protein. Amino acid substitutions may be conservative or non-conservative. Preferably, substitutions are conservative substitutions, in which one amino acid is substituted for another amino acid with similar structural and/or chemical properties. Additionally or alternatively, the variation may be by addition or deletion of 1, 2, 3, 4, 5, 6, 7, 8, 9, 10, 11, 12, 13, 14, 15, 16, 17, 18, 19, 20 or more amino acids within the protein.

Amino acid substitutions may be conservative or non-conservative. Preferably, substitutions are conservative substitutions, in which one amino acid is substituted for another amino acid with similar structural and/or chemical properties. Exemplary conservative substitutions are listed below.

Ala (A) val; leu; ile
Arg (R) lys; gin; asn
Asn (N) gln; his; lys
Asp (D) glu
Cys (C) ser
Gln (Q) asn
Glu (E) asp
Gly (G) pro; ala
His (H) asn; Gln; lys; arg
He (I) leu; val; met; ala
norleucine leu
Leu (L) norleucine; ile; met; ala; phe
Lys (K) arg; Gln; asn
Met (M) leu; phe; ile
Phe (F) leu; val; ile; ala; tyr
Pro (P) ala
Ser (S) thr
Thr (T) ser
Trp (W) tyr; phe
Tyr (Y) trp; phe; thr; ser
Val (V) ile; leu; met; phe; ala; norleucine Variant proteins may include proteins that have at least about 80% amino acid sequence identity with a polypeptide sequence disclosed herein. Preferably, a variant protein will have at least about 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a full-length polypeptide sequence or a fragment of a polypeptide sequence as disclosed herein. Amino acid sequence identity is defined as the percentage of amino acid residues in the variant sequence that are identical with the amino acid residues in the reference sequence, after aligning the sequences and introducing gaps, if necessary, to achieve the maximum percent sequence identity, and not considering any conservative substitutions as part of the sequence identity.

Sequence identity may be determined over the full length of the variant sequence, the full length of the reference sequence, or both. Methods for sequence alignment and determination of sequence identity are well known in the art, for example using publicly available computer software such as BioPerl, BLAST, BLAST-2, CS-BLAST, FASTA, ALIGN, ALIGN-2, LALIGN, Jaligner, matcher or Megalign (DNASTAR) software and alignment algorithms such as the Needleman-Wunsch and Smith-Waterman algorithms.

For example, the percentage identity may be calculated by performing a pairwise global alignment based on the Needleman-Wunsch alignment algorithm to find the optimum alignment (including gaps) of two sequences along their entire length, for instance using Needle, and using the BLOSUM62 matrix with a gap opening penalty of 10 and a gap extension penalty of 0.5.

Fragments of the proteins and variant proteins disclosed herein are also encompassed by the invention. Such fragments may be truncated at the N-terminus or C-terminus, or may lack internal residues, for example, when compared with a full length protein. Certain fragments lack amino acid residues that are not essential for enzymatic activity. Preferably, said fragments are at least about 10, 20, 30, 40, 50, 60, 70, 80, 90, 100, 110, 120, 150, 250, 300, 350, 400, 450, 500 or more amino acids in length.

Preferably, fragments and variants of sST2 retain a biological activity of the polypeptide with the amino acid sequence shown in SEQ ID No 1. Biological activity may include ability to bind IL-33.

sST2 Antagonist

An 'sST2 antagonist' or 'sST2-specific antagonist' refers to a molecule capable of neutralising, blocking, inhibiting, abrogating, reducing or interfering with sST2 expression or sST2 mediated biological activities including, but not limited to, its binding to one or more sST2 ligands, e.g. IL-33. sST2 antagonists include, without limitation, anti-sST2 antibodies and antigen-binding fragments thereof and small molecule inhibitors of sST2.

The term 'sST2 antagonist,' as used herein, may include molecules, including antibodies, antibody fragments, other binding polypeptides, peptides, and non-peptide small molecules, that bind to sST2 and are capable of neutralizing, blocking, inhibiting, abrogating, reducing or interfering with sST2 activities. The term 'sST2 activities' includes, for example, the ability of sST2 to bind to IL-33. The term 'sST2 antagonist,' may also include agents which reduce or block sST2 expression, such as sST2 antisense molecules or siRNAs.

In certain embodiments, the sST2 antagonist reduces or inhibits, by at least 10%, 20%, 30%, 40%, 50%, 60%, 70%, 80%, 90% or more, the expression level or biological activity of sST2. In certain embodiments, the sST2 antagonist reduces or inhibits binding of IL-33 to sST2 by, by at least 10%, 20%, 30%, 40%, 50%, 60%, 70%, 80%, 90% or more.

Controls

The expression of the sST2 in a biological sample from a subject may be compared with a control level. The control level may be, for example, a pre-determined control standard value or the expression level of sST2 in a control sample.

A control standard level may be obtained by measuring the level of sST2 in a suitable biological sample from a control subject or group of subjects, and where appropriate calculating an average or median level. The control subject or group of subjects may be, for example, a healthy subject, a group of healthy subjects, an HIV-infected subject, a group of HIV-infected subjects, or a randomly selected representative sample of subjects with or without history of any cardio vascular events (acute or chronic) (positive controls). Preferably, the subjects are human subjects. As used herein, 'healthy' refers to the absence of known disease or infection, in particular the absence of HIV infection and/or the absence of cardiovascular disease.

An increase or decrease in the level of expression of ST2 compared to a control may be expressed, for example, as a fold change or percentage of the control. The fold change in the subject sample compared to the control may be, without limitation, at least 1.2, at least 1.4, at least 1.6, at least 1.8, at least 2, at least 2.2, at least 2.4, at least 2.6, at least 2.8, at least 3, at least 3.5, at least 4, at least 4.5, at least 5, at least 6, at least 7 or at least 8-fold.

As will be clear to the skilled person, the nature of the control and/or the comparison, with the control and the conclusions drawn will depend on the nature of the control. For example, the control level may vary according to the type of biological sample used. The control level may also vary according to whether the subject has pre-existing cardiovascular disease or not. The control may also vary according to whether the subject is HIV-infected.

Similarly, an 'increased' or 'decreased' risk of mortality may be an increased or decreased risk compared to a control group as described above.

For example, in the case of a HIV-infected subject having pre-existing cardiovascular disease where the biological sample is whole blood, a suitable control reference level may be about 10, 20, 30, 40, 50, 60, 70, 80, 90, 95, 100, 110, 120, 130, 140, 150, 160, 170, 180, 190, or 200 pg/ml. In the case of a HIV-infected subject without pre-existing cardiovascular disease where the biological sample is whole blood, a suitable control reference level may be about 10, 20, 30, 40, 50, 60, 70, 80, 90, 95, 100, 110, 120, 130, 140, 150, 160, 170, 180, 190, or 200 pg/ml.

In the context of the present invention, the term 'overexpression' and 'overexpress' is intended to mean that the level of expression of sST2 is higher than that of the control. On the other hand, the term 'underexpression' and 'underexpress' is intended to mean that the level of expression of sST2 is lower than that of the control.

Detection of Protein Level

As used herein, 'sST2 level' or 'level of sST2' in a sample refers to the concentration or amount of sST2 in said sample. Preferably, protein concentration is measured. Protein concentration may be expressed, for example, in terms of weight/volume, for example pg/ml, ng/ml, pg/ml or mg/ml, or in terms of molarity, for example pM, nM, µM or mM in a given sample. The same applies to any other marker protein described herein.

The level of expression of the marker protein may be determined by gel electrophoresis (SDS-PAGE), in particular two-dimensional gel electrophoresis (2D-PAGE), carried out on the sample or a protein-containing extract thereof.

2D-PAGE is a well established technique in which proteins are first separated in one dimension by isoelectric focusing and further separated by SDS-PAGE along a second dimension. Protein expression may be analysed by visualization of labeled proteins, or by Western blotting and immune detection. Protein quantitation by 2D-PAGE is usually carried out by 2D-DiGE, in which proteins from a control sample and the test sample are labelled with different dyes. The dyes are mass- and charge-matched so the labeled proteins migrate to the same position on the gel, allowing quantification to be carried out within a single gel. Protein expression may also be determined by mass analysis, such as mass spectrometry. Qualitative and quantitative mass spectrometric techniques are known and used in the art. A quantitative LC-MS/MS can also be used.

Expression may also be determined using an antibody which binds to the protein, for example a monoclonal or polyclonal antibody, an antibody variant or fragments such as a single chain antibody, a diabody, a minibody, a single chain Fv fragment (sc(Fv)), a Sc(Fv)$_2$ antibody, a Fab fragment or a F(ab')$_2$ fragment, a V$_H$H antibody or a single domain antibody. The antibody may be mono-, bi-, tri- or multivalent. The antibody may be immobilized on a solid support. Antibodies may be used to determine protein expression in a range of immunological assays including competitive and non-competitive assay systems using techniques such as Western blotting, radioimmunoassay such as RIA (radio-linked immunoassay), ELISA (enzyme linked immunosorbent assay), 'sandwich' immunoassays, immunoprecipitation assays, immunodiffusion assays, agglutination assays, complement-fixation assays, immunoradiometric assays, fluorescent immunoassays, e.g. FIA (fluorescence-linked immunoassay), chemiluminescence immunoassays, electrochemiluminescence immunoassay (ECLIA) and protein A immunoassays. Such assays are routine and well known to the person skilled in the art.

Expression may alternatively be determined using a protein-specific aptamer. An aptamer is a short peptide capable of specifically binding to a specific protein sequence, consisting of a variable peptide loop attached at both ends to a protein scaffold. Methods for making protein aptamers are well known in the art, the most commonly used method being the yeast two-hybrid system. Such aptamers may preferably be labeled in order to allow the detection of a protein-ligand interaction. A nanotechnology-based assay could also be used.

For specific detection of sST2, commercially available ELISA assays may be used, such as that of ST2/IL-1R4 R&D systems (Oxford, UK; Ref DST200) or the ST2 ELISA available from MBL, Presage™ ST2 assay (Critical diagnostics)

Another tool for assessing sST2 levels is the Fluorokine® MAP multiplex kits (ref LUCA000), designed for use with the Luminex® 200™, flow-based sorting and detection analyzers.

Biological Sample

The biological sample may be, without limitation, whole blood, plasma, serum, saliva, urine or body tissue.

The biological sample is preferably taken before the commencement of therapy or before the planned commencement of therapy. For example, where the subject is HIV-infected, the sample is preferably taken before the commencement of anti-HIV therapy, such as antiretroviral therapy. The sample may also be taken after the commencement of therapy, for example after one round of therapy is completed in order to decide whether to proceed to further rounds.

Cardiovascular Disease

'Cardiovascular disease' (CVD) refers to the class of diseases affecting the cardiovascular system. Cardiovascular diseases include coronary heart disease (CHD), atherosclerotic non-CHD (stroke and peripheral arterial disease), 'Acute coronary syndrome' (ACS) and congestive heart failure (CHF).

'Coronary heart disease' means the failure of coronary circulation to supply adequate circulation to the cardiac muscle and surrounding tissue. This is usually a consequence of the narrowing of the blood vessels that supply blood to the heart. The cause is usually the build-up of atherosclerotic plaques in the coronary arteries, reducing blood flow to the heart.

'Congestive heart failure' means the pathological state in which an anomaly of the cardiac function is responsible for the heart being unable to pump blood sufficiently to satisfy the metabolic needs of the organism and/or in which the heart fulfils needs but with abnormally high filling pressures. In particular, it may relate to a left and/or right ventricular failure.

'Acute coronary syndrome' (ACS) relates to a group of coronary disorders that result from ischemic insult to the heart. ACS includes unstable angina, non-ST-elevation non-Q wave myocardial infarction (NSTEMI), ST-elevation non-Q wave myocardial infection (STEMI), and transmural (Q-wave) myocardial infarction. ACS can be divided into non-ST-elevation ACS (NSTEACS) and ST-elevation ACS (STEACS).

The expression 'non-ST-elevation acute coronary syndrome' refers to those ACS not associated with an elevated ST component in an electrocardiogram. Non-ST-elevation ACS include unstable angina and NSTEMI (see e.g. Nyman et al. (1993) *J. Intern. Med.* 234:293-301; Patel et al. (1996) *Heart* 75:222-228; Patel et al. (1998) *Eur. Heart J.* 19:240-49; and Lloyd-Jones et al. (1998) *Am. J. Cardiol.* 81:1182-86).

'Stroke' refers to a rapidly developing loss of brain functions due to a disturbance in the blood vessels supplying blood to the brain. Strokes can be classified in particular into ischemic stroke and hemorrhagic stroke. Ischemic strokes are those that are due to interruption of the blood supply, while hemorrhagic strokes are the ones which are due to rupture of a blood vessel or an abnormal vascular structure. As used herein, the term 'stroke' also includes transient ischemic attacks, also called TIA or 'mini stroke', which is a change in the blood supply to a particular area of the brain, resulting in brief neurologic dysfunction that persists, by definition, for less than 24 hours. 'Sepsis' is a condition characterised by a systemic inflammatory state and the presence of a known or suspected infection. This inflammatory state may arise as a consequence of the body's inflammatory response to infection at any site within the body. In severe sepsis, infection and systemic inflammation lead to organ dysfunction.

A cardiovascular event (CVE) may be any one of the above. Criteria for CVE events are described in Phillips et al, 2008, Antivir Ther 13:177. Reference to 'pre-existing cardiovascular disease' herein refers to subjects who have experienced at least one CVE, or who have ongoing disease such as CHD.

'Chronic lung disease' refers to chronic obstructive pulmonary disease (COPD), an umbrella term for a collection of chronic lung conditions which chronically obstruct the flow of air through the lungs and airways, creating difficulty breathing. The main conditions involved are chronic bronchitis and emphysema. The obstruction of air flow is usually permanent or semi-permanent and often progressive over time. The main symptom of COPD is shortness of breath (dyspnea). Other symptoms include cough, production of excess mucus, wheezing and chest tightness.

'Asthma' is a chronic lung disease which inflames and narrows the airways, causing wheezing, coughing, chest tightness and shortness of breath (dyspnea). Unlike in COPD, these symptoms are usually reversible and appear in response to triggers such as environmental pollution or physical effort. The symptoms are caused by bronchoconstriction, i.e. constriction of the muscles around the airways of the lungs, and inflammation of the airways. In severe cases, breathing is restricted to such an extent that death results.

'Allergy' or 'type I hypersensitivity' is a hypersensitivity disorder of the immune system. The immune system of allergic individuals reacts to substances which are harmless to most people ('allergens') by production of IgE leading to excessive activation of mast cells and basophils, leading to an inappropriate inflammatory response. The symptoms of allergy include asthma, itching, sneezing, dyspnea, rhinitis coughing and wheezing, skin rashes, and (in the case of food allergies) abdominal pain, vomiting and diarrhea. Severe allergies may result in death from anaphylaxis.

HIV Infection

A subject who is HIV-infected may have symptoms of disease as a consequence of infection, but may also be symptom free. HIV infection may thus need to be detected using one of the many assays known in the art.

Preferred assays for HIV infection include detection of anti-HIV antibodies in the subject's blood, serum or plasma. Many commercial assays for detection of anti-HIV antibodies are available. The most commonly used method is ELISA using enzyme conjugates that bind to specific HIV antibody, and substrates/chromogens that produce colour in a reaction catalyzed by the bound enzyme conjugate. Western blotting may also be used.

The most popular ELISA involves an indirect method in which HIV antigen is immobilised and antibody in the sample is allowed to react with the antigen-coated support. Several indirect ELISA tests incorporate polyvalent conjugates (anti-IgG and anti-IgM) and antigen-sandwich configurations in order to increase sensitivity for detecting early infection.

An 'HIV seropositive' subject has antibodies to human immunodeficiency virus (HIV) in their bloodstream. HIV seropositivity is diagnostic of HIV infection, in particular established HIV infection.

There are limitations to tests in which anti-HIV antibody is detected, as specific antibody to HIV is produced shortly after infection, but the exact time depends on several factors, including host and viral characteristics. Importantly, antibody may be present at low levels during early infection but not at the detection limit of some assays.

Other assays which may be used include detection of the presence of HIV antigens, either using anti-HIV antibody or by detecting HIV nucleic acid, either RNA or DNA. Detection of HIV antigens is usually based on detection of circulating viral protein p24.

Assays which simultaneously test for HIV antibody and antigen are also available, and include include the VIDAS HIV DUO Ultra (bioMérieux; Marcy l'Etoile, France), Enzymun-Test-HIV-Combi (Boehringer; Mannheim, Germany), Vironostika HIV Uni-Form II Ag/AB (Organon Teknika; Boxtel, Netherlands), AxSYM-HIV Ag/AB (Abbott Laboratories; Abbott Park, Ill.), Enzygnost HIV Integral (Dade Behring; Marburg, Germany), Genescreen Plus HIV Ag-AB (Bio-Rad), and COBAS Core HIV Combi (Roche Diagnostics; Mannheim, Germany).

The 'window period' before the detection of antibody can be shortened by several days using antigen tests, and by several more days using nucleic acid detection methods. Therefore, in most individuals, the window period may be only 2-3 weeks if an all-inclusive testing strategy is used. Most antibody tests currently on the market have equivalent degrees of sensitivity for detecting most individuals who are infected with HIV (epidemiologic sensitivity), but they vary in their ability to detect low levels of antibody (analytical sensitivity).

Diagnosis, Prognosis and Treatment

The term 'diagnosis' is used herein to refer to the identification of a molecular or pathological state, disease or condition, such as the identification of HIV or cardiovascular disease or to refer to identification of a HIV or cardiovascular disease subject who may benefit from a particular treatment regimen.

The term 'prognosis' is used herein to refer to the prediction of the course of a disease and/or to the prediction of the likelihood of benefit from therapy. In preferred embodiments; prognosis may include predicting the likelihood of death or admission to hospital within a certain time period. The term 'prediction' or 'predicting' may refer to the likelihood that a patient will respond either favourably or unfavourably to a particular therapy. In one embodiment, prediction or predicting relates to the extent of those responses. In one embodiment, the prediction or predicting relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favourably to a treatment regimen, such as a given therapeutic regimen, or whether long-term survival of the patient following a therapeutic regimen is likely.

Reference to an 'improved' prognosis, a 'poor' prognosis, an 'increased risk' of mortality and the like, as used herein, is preferably in comparison to a control subject group as defined above. In some embodiments, said control subject group is the same subject group as that used to provide the control or control reference level used for the sST2 comparison.

The time period may be, for example, 1, 2, 3, 4, 5, 6, 7, 8, 9, 10, 11 or 12 months, or 1, 2, 3, 4, 5, 6, 7, 8, 9, or 10 years or more.

'Treatment' includes both therapeutic treatment and prophylactic or preventative treatment, wherein the object is to prevent or slow down the targeted pathologic condition or disorder. Those in need of treatment include those already with the disorder as well as those prone to have the disorder or those in whom the disorder is to be prevented. The terms 'therapy', 'therapeutic', 'treatment' or 'treating' include reducing, alleviating or inhibiting or eliminating the symptoms or progress of a disease, as well as treatment intended to reduce, alleviate, inhibit or eliminate said symptoms or progress. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, methods and compositions of the invention are used to delay development of a disease or disorder or to slow the progression of a disease or disorder.

Treatment in accordance with the invention includes a method of treating a cardiovascular disease comprising administration of an sST2 antagonist as described herein. Preferably, an effective amount, preferably a therapeutically effective amount of said antagonist is administered. An 'effective amount' refers to an amount effective, at dosages and for periods of time necessary, to achieve the desired therapeutic or prophylactic result.

A 'therapeutically effective amount' of said antagonist may vary according to factors such as the disease state, age, sex, and weight of the subject, and the ability of the protein, to elicit a desired therapeutic result. A therapeutically effective amount encompasses an amount in which any toxic or detrimental effects of the protein are outweighed by the therapeutically beneficial effects. A therapeutically effective amount also encompasses an amount sufficient to confer benefit, e.g., clinical benefit.

Treatment of cardiovascular disease may include surgical intervention, such as coronary bypass procedures, valve repair or replacement, insertion of stents and heart transplant operations. Additionally or alternatively, said treatment may include use of drugs such as angiotensin receptor blockers, ACE inhibitors, anttiarrhythmics, antiplatelet therapy, aspirin, beta-blockers, calcium channel blockers, anti-thrombotic agents, cholesterol lowering agents such as statins, bigitalis medicines, diuretics, inotropic agents and nitrates. Lifestyle changes such as increased exercise, stress reduction techniques, weight loss and dietary improvements may also be recommended. An aggressive treatment may include one or more surgical procedures, and/or use of a multiple drug regime. A conservative treatment may include only lifestyle changes and/or use of selected drugs only.

The following examples and figures illustrate the invention, without limiting the scope of the claims.

All literature references cited herein are hereby incorporated by reference in their entirety.

EXPERIMENTAL SECTION

Methods
Cross-Sectional Study of Samples from HIV-Infected Patients and Healthy Donors In the cross-sectional study, 116 men and 38 female were enrolled from one center in Henri Mondor Hospital (Créteil, France). The study was approved by the local ethics committee. Blood was collected in tubes containing EDTA (potassium ethylenediamine tetra-acetic acid) for viral load and sST2. To establish reference values for sST2 biomarker, 35 HIV-uninfected healthy donors 21-73 years of age with BMI between 19.9 and 36.7 were recruited.

SMART Study Samples

The methods and results of the SMART trial have been published (El-Sadr et al, 2006, N Engl J Med 355:2283). Between January 2002 and January 2006, 5472 HIV-infected patients with a $CD4^+$ cell count above 350 cells/µl were randomized to episodic ART (drug conservation) or continuous ART (viral suppression). Viral suppression patients taking ART at entry continued taking it, and those not taking it initiated ART after randomization. For the viral suppression group, available ART was to be used in an uninterrupted manner with the goal of maximal and continuous suppression of HIV replication. The experimental drug conservation strategy entailed intermittent use of ART for periods defined by $CD4^+$ cell count until January 2006, at which time the study participants were advised to reintroduce ART due to an increased risk of opportunistic disease and risk. Patients were asked to consent to storing blood for future research, and only samples for consenting patients were used. The SMART study was approved by the ethics committee of each clinical site and of the University of Minnesota.

Criteria for CVD events, defined as coronary heart disease (CHD), atherosclerotic non-CHD (stroke and peripheral arterial disease), congestive heart failure (CHF) and CVD or unwitnessed death, have been previously described (Phillips et al, 2008, Antivir Ther 13:177). For CVD cases with a blood specimen available for analysis (216 patients) and for controls (n=399) matched on the country, age, sex, sST2 was measured at baseline (study entry) on stored serum.

Biomarker Methods sST2 assays were performed by ELISA (ST2/IL-1R4 R&D systems, Oxford, UK) according to the manufacturer's instructions with a coefficient of variation <10% and a lower limit of detection of 2 pg/ml and a upper limit of detection >2000 pg/ml. All samples were analyzed blinded to case and control status and to treatment group.

Statistical Methods

Odd ratios (OR) associated with baseline levels of sST2 for CVD were estimated using conditional logistic regression. Models which adjusted for race, use of HAART, viral load, smoking, prior CVD, metabolic factors, co-infection, major ECG abnormalities, hsCRP, IL-6 and D-dimer in addition to matching factors were considered as well as unadjusted models (matching factors only).

Results
sST2 is Increased in HIV Infected Patients

Figure 1:
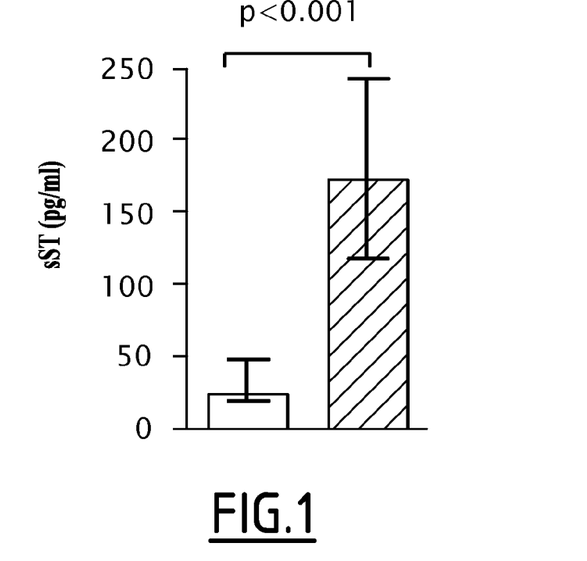
FIG. 1 shows sST2 levels (pg/ml) in healthy donors (open bar) versus HIV-infected subjects (filled bar).
Figure 2:
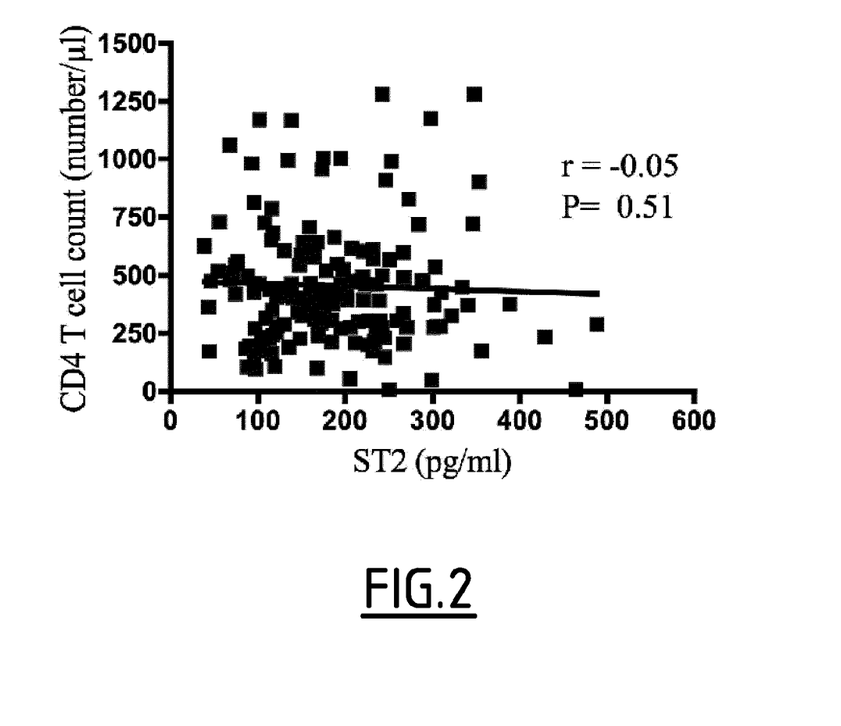
FIG. 2 shows CD4 cell count versus ST2 level (pg/ml).
Figure 3:
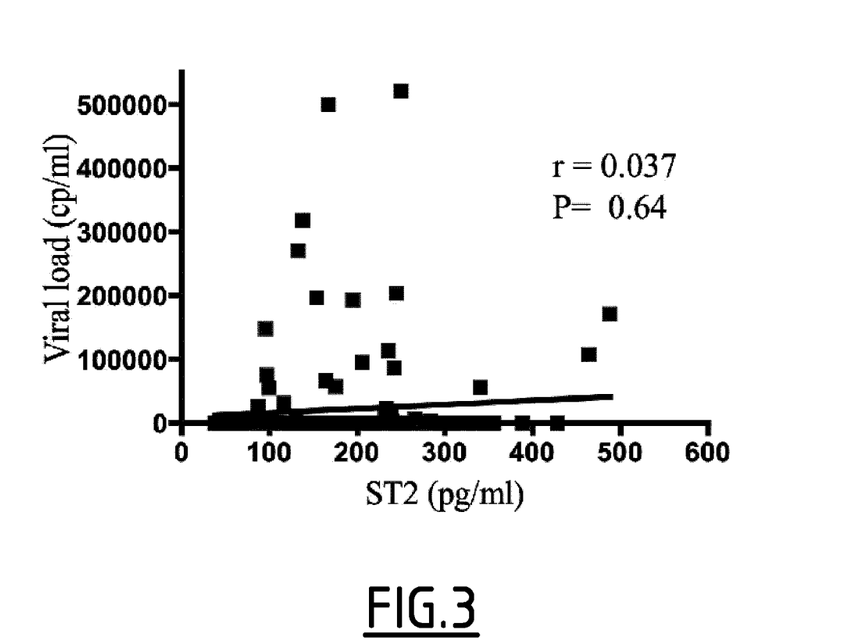
FIG. 3 shows viral load versus ST2 level (pg/ml).

Serum sST2 levels were analyzed in 131 HIV infected patients and 35 healthy volunteers. As shown in FIG. 1, serum sST2 concentration, expressed as median (interquartile range [IQR]) is significantly higher in HIV infected patients (174.8 pg/ml [IQR 129.9 to 235.3] than in the healthy volunteers (24.9 pg/ml [IQR 20.3 to 48.05]; $p<0.001$). sST2 does not correlate with age (data not shown). The relationships between sST2, viral load and $CD4^+$ T cell count are shown in FIGS. 2 and 3. No association is found with $CD4^+$ T count ($r=-0.05$, $p=0.51$) and viral load ($r=0.037$, $p=0.64$).

Figure 4:
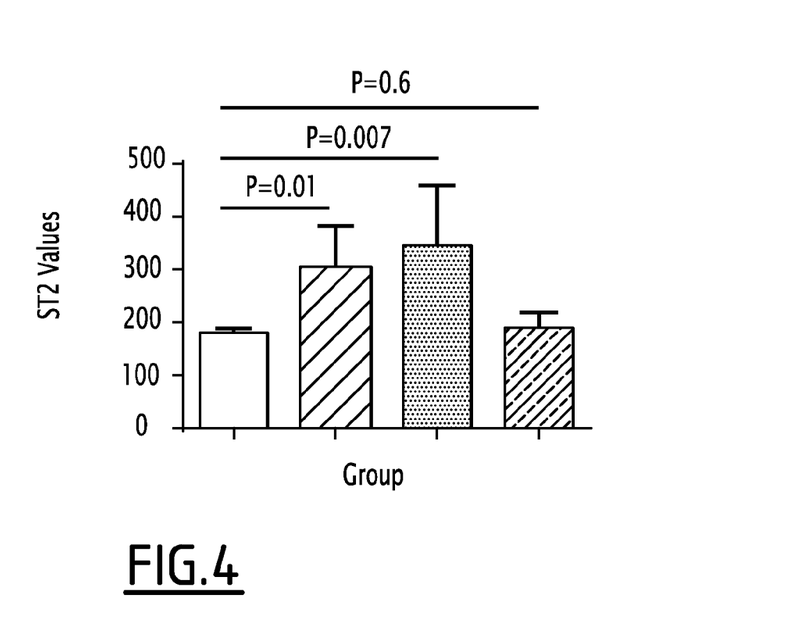
FIG. 4 shows ST2 values in subjects with no history of CVE (cardiovascular event; open bar) and those with history of CVE (filled bar). The dark grey bars show ST2 level in CVE subjects in which a CVE occurred before ST2 measurement. The light grey bars show ST2 levels in subjects in which a CVE occurred after ST2 measurement.

Among these 131 infected patients, 21 patients had a cardiovascular event (CVE) either before or after sST2 measurement (12 myocardial infarctions, 4 ischemic strokes, 2 peripheral vascular diseases, 2 left ventricular insufficiency, 1 pulmonary hypertension). As previously reported for HIV negative patients, a clear association between history of CVE and elevated levels of sST2 in HIV infected patients is observed (FIG. 4). However, when a CVE event occurred before sST2 measurement, the highest sST2 levels were observed, suggesting that sST2 may be a predictive factor of CVD.

sST2 is Correlated with Cardiovascular Disease Mortality in HIV-Infected Subjects Table 1 gives baseline characteristics for CVD cases and matched controls in HIV-infected subjects. In univariate analyses, prior AIDS, current smoking status, diabetes, prior CVD, major resting ECG abnormality and use of blood pressure lowering drugs were associated with an increased risk of CVD. In addition, HDL cholesterol was lower in CVD cases compared to controls. Baseline hsCRP, IL-6 and D-dimer were significantly higher in CVD cases than controls. At baseline, median sST2 level was 85.0 pg/ml (IQR 24 to 247) in patients who developed a CVD event and 78.0 pg/ml (IQR 22 to 208) in the matched control patients. There was no difference in median sST2 levels with age, gender and co-infection with hepatitis B/C. No difference was observed in median ST2 levels by time of CVD event.

As in the first study, there was no association between sST2 and CD4+ T count (r=−0.02, p=0.6) and HIV RNA levels (r=−0.03, p=0.39). At baseline, sST2 were correlated with IL-6 (r=0.11, p=0.008). However, there was no association between sST2 and hsCRP (r=0.05, p=0.26) and D-dimer (r=0.07, p=0.09). A significant correlation were found between sST2 and HDL-cholesterol (r=−0.09, p=0.03) and total/HDL ratio (r=0.10, p=0.02). There was a significant correlation between sST2 and triglycerides (r=0.08, p=0.04) and Apo/Apo A1 Ration (r=0.09, p=0.03).

TABLE 1

Baseline Characteristics, cardiovascular disease risk factors and lipid profile of cardiovascular disease cases and matched controls with ST2 results

|  | CVD Cases (N = 216) | Controls (N = 399) | P-value* |
|---|---|---|---|
| Treatment group (% DC) | 56.5 | 45.6 | 0.01 |
| Demographics |  |  |  |
| Age (median, IQR) | 50 (44, 56) | 49 (43, 56) | NA |
| Gender (% female) | 18.1 | 17.8 | NA |
| Black (%) | 38.0 | 37.1 | 0.90 |
| CD4+ (cells/mm³) (median, IQR) | 576 (456, 839) | 635 (483, 803) | 0.73 |
| CD4+ nadir (cells/mm³) (median, IQR) | 233 (117, 351) | 244 (148, 346) | 0.81 |
| HIV-RNA ≤ 400 copies/mL (%) | 67.0 | 66.8 | 0.93 |
| Prior AIDS-related illnesses (%) | 37.5 | 25.1 | 0.001 |
| Hepatitis B (%) | 1.4 | 1.3 | 0.80 |
| Hepatitis C (%) | 20.8 | 20.3 | 0.83 |
| CVD Risk Factors |  |  |  |
| Current smoker (%) | 52.3 | 40.9 | 0.009 |
| Diabetes (%) | 16.7 | 9.8 | 0.01 |
| Prior CVD (%) | 13.9 | 5.5 | <0.001 |
| Major ECG abnormality (%) | 21.2 | 10.5 | <0.001 |
| Blood pressure lowering drugs (%) | 44.0 | 31.6 | 0.001 |
| Lipid lowering drugs (%) | 28.7 | 24.3 | 0.29 |
| Lipids |  |  |  |
| Total cholesterol (mg/dl) (median, IQR) | 195 (169, 233) | 193 (168, 232) | 0.77 |
| HDL cholesterol (mg/dl) (median, IQR) | 38 (31, 48) | 42 (33, 52) | 0.03 |
| LDL cholesterol (mg/dl) (median, IQR) | 111 (88, 141) | 110 (89, 134) | 0.80 |
| Triglycerides (mg/dl) (median, IQR) | 190 (133, 312) | 181 (124, 300) | 0.59 |
| Total/HDL cholesterol (median, IQR) | 5.5 (3.9, 6.9) | 4.7 (3.5, 6.1) | 0.17 |
| Biomarkers |  |  |  |
| hsCRP (μg/mL) (median, IQR) | 3.66 (1.54, 7.75) | 2.18 (0.92, 4.93) | <0.001 |
| IL-6 (pg/mL) (median, IQR) | 3.20 (1.98, 4.91) | 2.22 (1.44, 3.53) | <0.001 |
| D-dimer (μg/mL) (median, IQR) | 0.31 (0.20, 0.60) | 0.24 (0.15, 0.47) | 0.001 |
| ST2 (pg/mL) (median, IQR) | 85 (24, 247) | 78 (22, 208) | 0.35 |

*P-value obtained from univariate conditional logistic model. Biomarkers are natural log transformed Table 2 summarizes the ORs of the upper quartiles versus the lower quartile of sST2. The unadjusted OR for CVD for the highest quartile (4.2% of cases and 4% of controls) versus lower quartile (12.5% of cases and 15.3% of controls) was 1.2 (95% CI: 0.8 to 2.5; p=0.22). After adjustment for baseline covariates this OR was 1.6 (95% CI: 0.8 to 3.2; p=0.19). Moreover, after adjustment for covariates that also included baseline levels of $\log_e$ IL-6, hsCRP and D-dimer, this OR was 1.7 (95% CI: 0.8-3.6, p=0.2).

TABLE 2

Odds ratio for cardiovascular disease for upper versus lower quartile of ST2 levels

| ST2 level (pg/mL) | OR (95% CI) | p-value |
|---|---|---|
| Unadjusted |  |  |
| <2 (ref.) | — | — |
| 2-22 | 1.4 (0.7-3.0) | 0.33 |
| 23-79 | 1.2 (0.6-2.1) | 0.62 |
| 80-221 | 1.2 (0.7-2.1) | 0.59 |
| 222+ | 1.4 (0.8-2.5) | 0.22 |
| Adjusted (1) |  |  |
| <2 (ref.) | — | — |
| 2-22 | 1.8 (0.8-4.1) | 0.16 |
| 23-79 | 1.1 (0.6-2.3) | 0.71 |
| 80-221 | 1.2 (0.6-2.3) | 0.61 |
| 222+ | 1.6 (0.8-3.2) | 0.19 |
| Adjusted (2) |  |  |
| <2 (ref.) | — | — |
| 2-22 | 1.7 (0.7-4.2) | 0.27 |
| 23-79 | 1.0 (0.5-2.1) | 0.97 |
| 80-221 | 1.0 (0.5-2.2) | 0.97 |
| 222+ | 1.7 (0.8-3.6) | 0.20 |

(1) adjusted for age, race, ART and HIV-RNA, smoking, prior CVD, diabetes, BP lowering drugs, total/HDL cholesterol, CD4+, BMI and major ECG abnormalities
(2) adjusted for (1) plus $\log_e$ hsCRP, IL-6 and D-dimer Median sST2 for cases and controls by type of event are given in Table 3. Of the 216 CVD events, 53 patients died. Thirty three of the deaths were not preceded by a non-fatal event. Twenty deaths were preceded by a non-fatal event. Median sST2 levels are particularly high among patients who died. Median sST2 was 114 pg/ml (IQR 37 to 359) in patients who died without history of CVD as compared to 78 pg/ml (IQR 32 to 149) in matched controls, and 158 pg/ml (IQR 48 to 289) in patients who died with history of CVD as compared to 94 pg/ml (IQR 27 to 228) in matched controls. For the patients suffering non-fatal events that did not subsequently die (163 cases of 216 CVD cases), there were no differences between sST2 levels for cases (72 pg/ml; [IQR 23 to 222]) and matched controls (77 pg/ml; [IQR 20 to 220]). Moreover, the unadjusted OR was greater when only the 33 CVD/unwitnessed deaths were considered: 2.8 (95% CI: 0.8 to 10.3; p=0.12).

TABLE 3

ST2 levels (pg/ml) by CVD event/death and case history of CVD or CHF

|  | Cases | | Matched Controls | |
| --- | --- | --- | --- | --- |
|  | N | Median (IQR) | N | Median (IQR) |
| CVD or unwitnessed deaths | | | | |
| Overall | 33 | 114 (37, 359) | 61 | 78 (32, 149) |
| Prior CVD | 8 | 114 (43, 158) | 15 | 106 (52, 157) |
| Prior CHF | 3 | 102 (85, 179) | 6 | 128 (62, 208) |
| No prior CVD or CHF | 24 | 136 (35, 498) | 44 | 68 (18, 146) |
| Non-fatal CVD and subsequently died | | | | |
| Overall | 20 | 158 (48, 289) | 37 | 94 (27, 228) |
| Prior CVD | 3 | 16 (2, 275) | 6 | 84 (48, 119) |
| Prior CHF | 2 | 140 (4, 275) | 4 | 54 (28, 144) |
| No prior CVD or CHF | 16 | 170 (91, 336) | 29 | 94 (27, 366) |
| Non-fatal CVD and did not die | | | | |
| Overall | 163 | 72 (23, 222) | 301 | 77 (20, 220) |
| Prior CVD | 19 | 91 (50, 107) | 35 | 70 (8, 286) |
| Prior CHF | 2 | 1054 (107, 2000) | 3 | 68 (2, 2000) |
| No prior CVD or CHF | 144 | 69 (22, 225) | 266 | 77 (22, 220) |

The invention claimed is:

1. A method of predicting a risk of mortality within one year following a cardiovascular event, of an HIV-infected subject, and, based on the risk of mortality, treating the HIV-infected subject using a suitable method, comprising
   (i) measuring, in an HIV-infected subject who has no pre-existing cardiovascular disease and who has not yet commenced anti-HIV therapy, a level of sST2 in a biological sample from said subject,
   (ii) comparing said level of sST2 with a control level derived from HIV-infected subjects with no pre-existing cardiovascular disease, wherein a level of sST2 in the subject sample which is higher than that of the control is indicative of an increased risk of mortality; and
   (iii) treating the HIV-infected subject with an aggressive cardiovascular disease treatment when an elevated level of sST2 is detected in the subject sample compared to the control and treating the HIV-infected subject with a conservative cardiovascular disease treatment when the level of sST2 detected in the subject sample is not elevated compared to the control.

2. The method of claim 1, wherein the biological sample is whole blood, plasma or serum.

3. The method of claim 1, wherein the aggressive treatment is one or both of surgical intervention and administering a multiple drug regime, and wherein the conservative treatment comprises one or both of lifestyle changes and administering a selected drug.

4. The method of claim 3, wherein the surgical intervention is selected from the group consisting of a coronary bypass procedure, valve repair or replacement, insertion of one or more stents and a heart transplant operation.

5. The method of claim 3, wherein the multiple drug regime includes two or more drugs selected from the group consisting of angiotensin receptor blockers, ACE inhibitors, anti-arrhythmics, antiplatelet therapeutics, aspirin, beta-blockers, calcium channel blockers, anti-thrombotic agents, cholesterol lowering agents, digitalis medicines, diuretics, inotropic agents and nitrates and the selected drug is a single drug selected from the group consisting of angiotensin receptor blockers, ACE inhibitors, anti-arrhythmics, anti-platelet therapeutics, aspirin, beta-blockers, calcium channel blockers, anti-thrombotic agents, cholesterol lowering agents, digitalis medicines, diuretics, inotropic agents and nitrates.

6. The method of claim 3, wherein the lifestyle changes are selected from the group consisting of increased exercise, stress reduction techniques, weight loss, dietary improvements increased exercise, stress reduction techniques, weight loss and dietary improvements.

* * * * *

SEQUENCE LISTING

<160> NUMBER OF SEQ ID NOS: 2

<210> SEQ ID NO 1
<211> LENGTH: 556
<212> TYPE: PRT
<213> ORGANISM: Homo sapiens

<400> SEQUENCE: 1

```
Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220
```

-continued

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
            245                 250                 255

Lys Ile Thr Asp Phe Gly Glu Pro Arg Ile Gln Gln Glu Glu Gly Gln
        260                 265                 270

Asn Gln Ser Phe Ser Asn Gly Leu Ala Cys Leu Asp Met Val Leu Arg
    275                 280                 285

Ile Ala Asp Val Lys Glu Asp Leu Leu Leu Gln Tyr Asp Cys Leu
290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ala Val Cys
            325                 330                 335

Ser Val Phe Leu Met Leu Ile Asn Val Leu Ile Ile Leu Lys Met
            340                 345                 350

Phe Trp Ile Glu Ala Thr Leu Leu Trp Arg Asp Ile Ala Lys Pro Tyr
            355                 360                 365

Lys Thr Arg Asn Asp Gly Lys Leu Tyr Asp Ala Tyr Val Val Tyr Pro
370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
            405                 410                 415

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
            435                 440                 445

Thr Pro Gln Ile Thr His Asn Lys Glu Phe Ala Tyr Glu Gln Glu Val
450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
            485                 490                 495

Gln Asp Ser Leu Gln His Leu Met Lys Val Gln Gly Thr Ile Lys Trp
            500                 505                 510

Arg Glu Asp His Ile Ala Asn Lys Arg Ser Leu Asn Ser Lys Phe Trp
            515                 520                 525

Lys His Val Arg Tyr Gln Met Pro Val Pro Ser Lys Ile Pro Arg Lys
530                 535                 540

Ala Ser Ser Leu Thr Pro Leu Ala Ala Gln Lys Gln
545                 550                 555

<210> SEQ ID NO 2
<211> LENGTH: 328
<212> TYPE: PRT
<213> ORGANISM: Homo sapiens

<400> SEQUENCE: 2

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

```
Tyr Tyr Ser Gln Thr Asn Lys Ser Ile Pro Thr Gln Glu Arg Asn Arg
    50              55              60

Val Phe Ala Ser Gly Gln Leu Leu Lys Phe Leu Pro Ala Ala Val Ala
65              70              75              80

Asp Ser Gly Ile Tyr Thr Cys Ile Val Arg Ser Pro Thr Phe Asn Arg
                85              90              95

Thr Gly Tyr Ala Asn Val Thr Ile Tyr Lys Lys Gln Ser Asp Cys Asn
                100             105             110

Val Pro Asp Tyr Leu Met Tyr Ser Thr Val Ser Gly Ser Glu Lys Asn
            115             120             125

Ser Lys Ile Tyr Cys Pro Thr Ile Asp Leu Tyr Asn Trp Thr Ala Pro
130             135             140

Leu Glu Trp Phe Lys Asn Cys Gln Ala Leu Gln Gly Ser Arg Tyr Arg
145             150             155             160

Ala His Lys Ser Phe Leu Val Ile Asp Asn Val Met Thr Glu Asp Ala
                165             170             175

Gly Asp Tyr Thr Cys Lys Phe Ile His Asn Glu Asn Gly Ala Asn Tyr
            180             185             190

Ser Val Thr Ala Thr Arg Ser Phe Thr Val Lys Asp Glu Gln Gly Phe
    195             200             205

Ser Leu Phe Pro Val Ile Gly Ala Pro Ala Gln Asn Glu Ile Lys Glu
    210             215             220

Val Glu Ile Gly Lys Asn Ala Asn Leu Thr Cys Ser Ala Cys Phe Gly
225             230             235             240

Lys Gly Thr Gln Phe Leu Ala Ala Val Leu Trp Gln Leu Asn Gly Thr
            245             250             255

Lys Ile Thr Asp Phe Gly Glu Pro Arg Ile Gln Gln Glu Glu Gly Gln
            260             265             270

Asn Gln Ser Phe Ser Asn Gly Leu Ala Cys Leu Asp Met Val Leu Arg
        275             280             285

Ile Ala Asp Val Lys Glu Glu Asp Leu Leu Leu Gln Tyr Asp Cys Leu
        290             295             300

Ala Leu Asn Leu His Gly Leu Arg Arg His Thr Val Arg Leu Ser Arg
305             310             315             320

Lys Asn Pro Ser Lys Glu Cys Phe
                325
```